(12) United States Patent
Beer

(10) Patent No.: US 10,940,964 B2
(45) Date of Patent: Mar. 9, 2021

(54) DEVICE AND METHOD FOR FILLING AN ELECTRIC CIGARETTE

(71) Applicant: Fontem Holdings 1 B.V., Amsterdam (NL)

(72) Inventor: Andreas Beer, Grasbrunn (DE)

(73) Assignee: Fontem Holdings 1 B.V., Amsterdam (NL)

( * ) Notice: Subject to any disclaimer, the term of this patent is extended or adjusted under 35 U.S.C. 154(b) by 182 days.

(21) Appl. No.: 15/759,450

(22) PCT Filed: Sep. 15, 2016

(86) PCT No.: PCT/EP2016/071829
§ 371 (c)(1),
(2) Date: Apr. 26, 2018

(87) PCT Pub. No.: WO2017/046247
PCT Pub. Date: Mar. 23, 2017

(65) Prior Publication Data
US 2018/0257797 A1     Sep. 13, 2018

(30) Foreign Application Priority Data
Sep. 15, 2015   (DE) ..................... 10 2015 217 671.1

(51) Int. Cl.
*B65B 3/12*     (2006.01)
*A24F 47/00*   (2020.01)
(Continued)

(52) U.S. Cl.
CPC ............. *B65B 3/12* (2013.01); *A24F 47/008* (2013.01); *B65B 3/003* (2013.01); *B65B 3/18* (2013.01); *A61M 2209/045* (2013.01)

(58) Field of Classification Search
None
See application file for complete search history.

(56) References Cited

U.S. PATENT DOCUMENTS

| | | | |
|---|---|---|---|
| 7,922,699 B2 * | 4/2011 | Baba | A61M 5/31596 604/220 |
| 2010/0242975 A1 | 9/2010 | Hearn | |

(Continued)

FOREIGN PATENT DOCUMENTS

| | | |
|---|---|---|
| GB | 2522396 A | 7/2015 |
| WO | 2011095781 A1 | 8/2011 |

(Continued)

*Primary Examiner* — Daphne M Barry
(74) *Attorney, Agent, or Firm* — Dykema Gossett PLLC

(57) ABSTRACT

The invention discloses a device for filling an electric cigarette, more specifically for filling a consumable-material tank of an electric cigarette wherein the device has a first tank for accommodating a consumable material and a second tank for accommodating air, wherein the device is designed such that the volumes of the tanks can be altered inversely by means of an actuating device, and therefore a pressing action and an intake action can be established at connections of the tanks. By virtue of the device being connected to a consumable-material tank of an electric cigarette, it is thus possible, while the consumable-material tank is being filled with consumable material, for the air displaced by the consumable material to be simultaneously extracted from the electric cigarette.

17 Claims, 20 Drawing Sheets

(51) Int. Cl.
*B65B 3/00* (2006.01)
*B65B 3/18* (2006.01)

(56) References Cited

U.S. PATENT DOCUMENTS

| | | | | |
|---|---|---|---|---|
| 2013/0035658 A1* | 2/2013 | Haenggi | ............ | A61J 1/20 |
| | | | | 604/408 |
| 2015/0245654 A1* | 9/2015 | Memari | ............ | H02J 7/025 |
| | | | | 141/2 |
| 2016/0037826 A1* | 2/2016 | Hearn | ............ | B65D 83/48 |
| | | | | 141/3 |

FOREIGN PATENT DOCUMENTS

| WO | 2012070107 A1 | 5/2012 |
|---|---|---|
| WO | 2014155092 A1 | 10/2014 |

\* cited by examiner

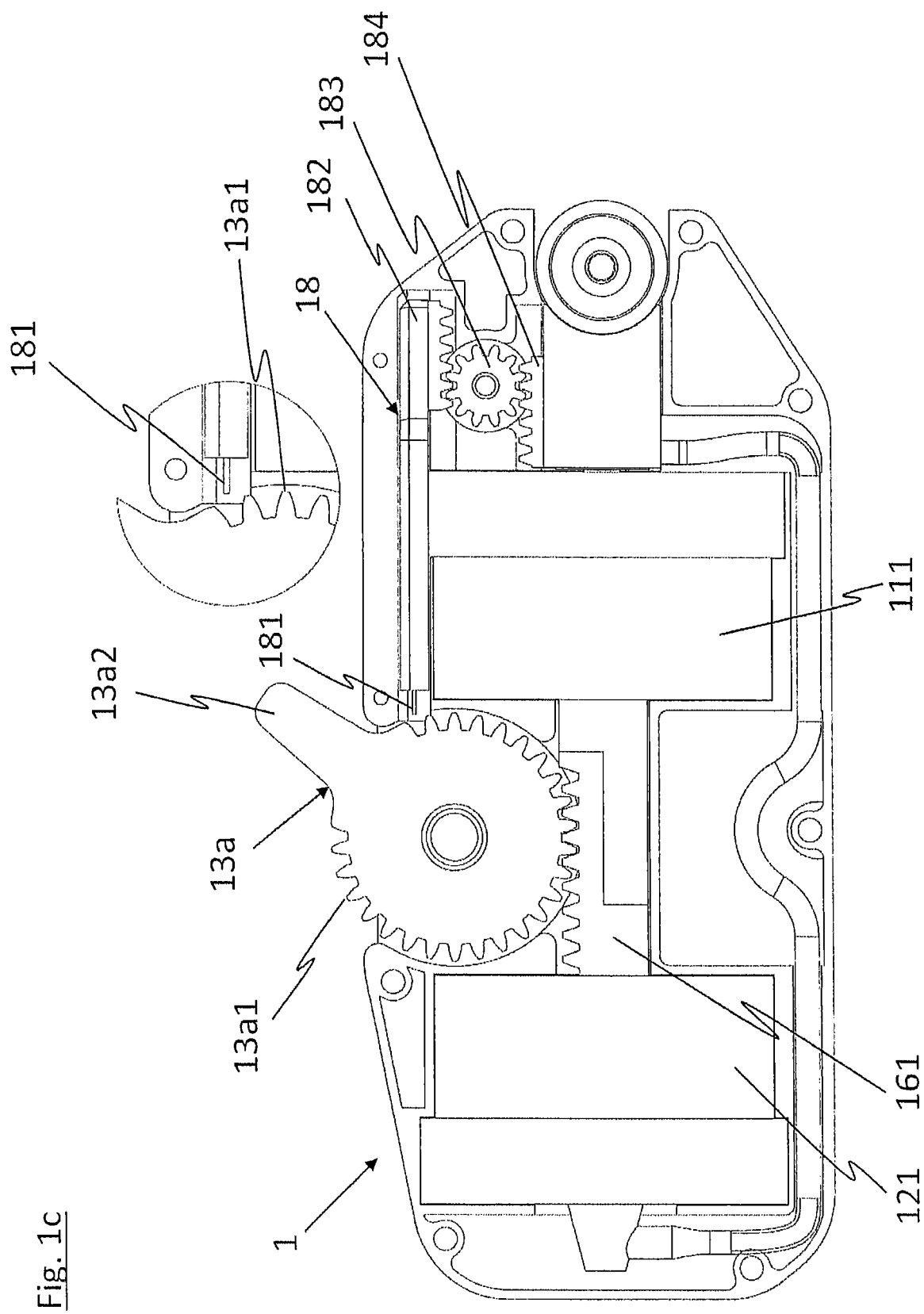

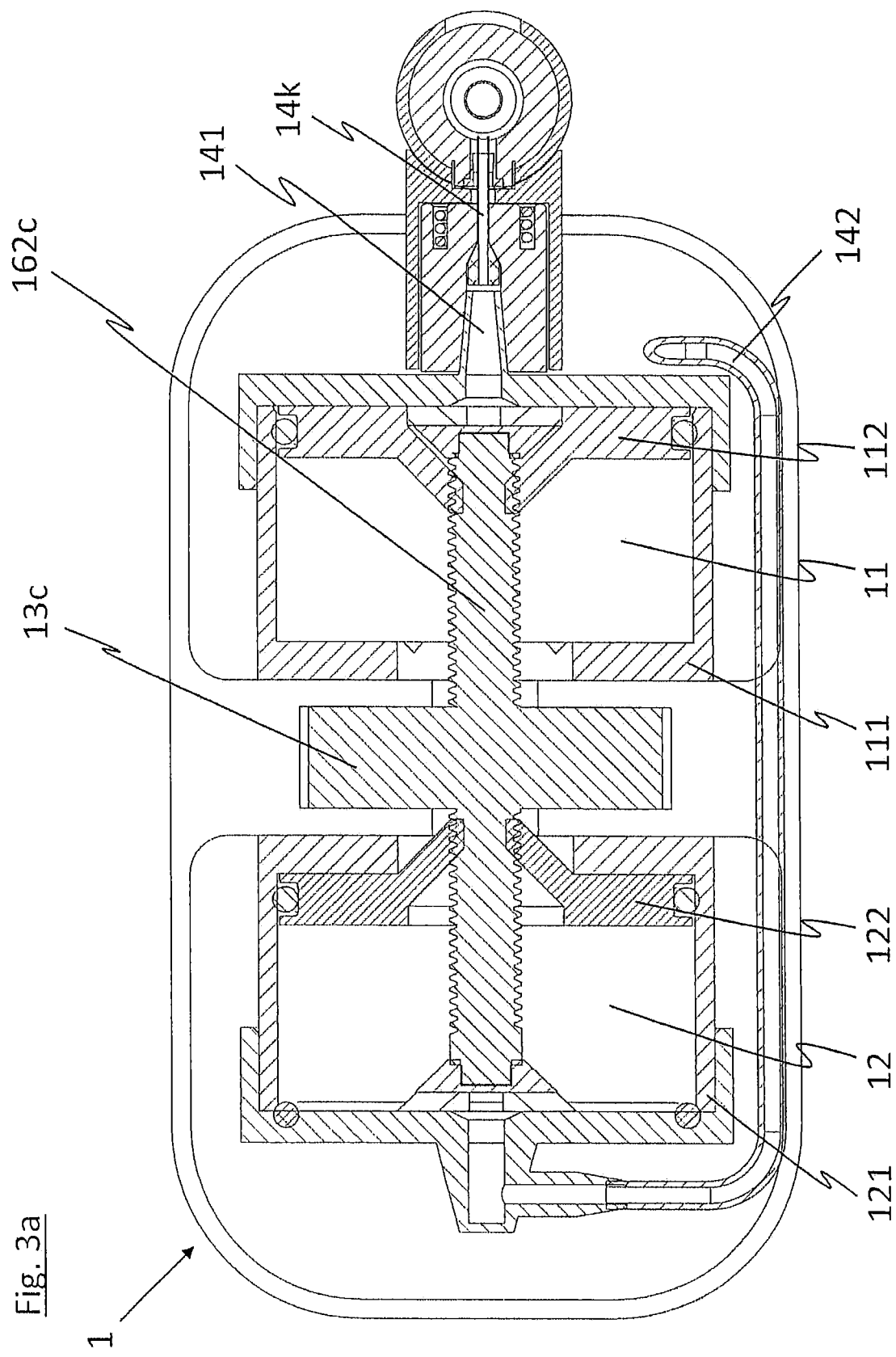

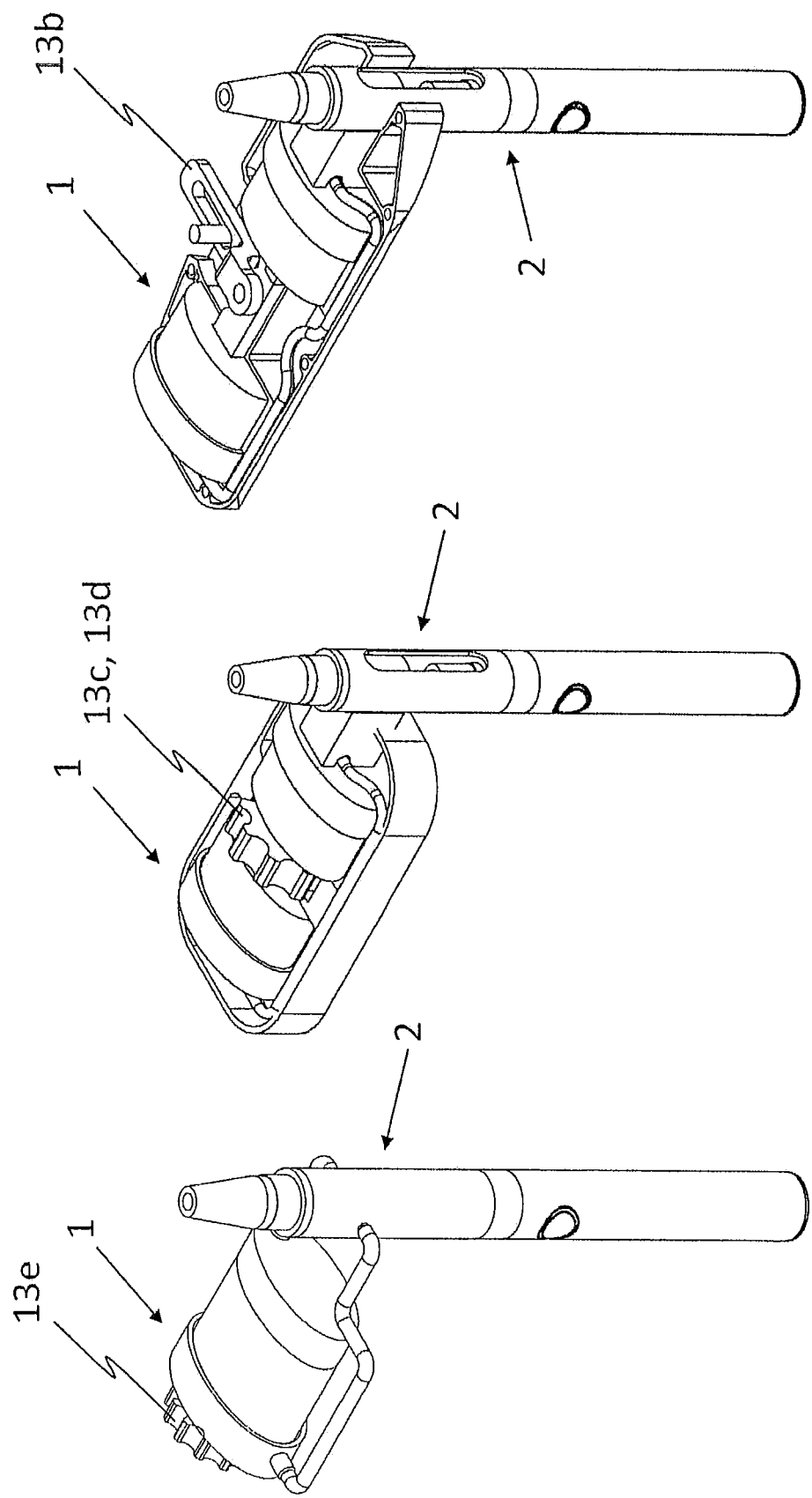

DEVICE AND METHOD FOR FILLING AN ELECTRIC CIGARETTE

The invention relates to a device for filling an electric cigarette, a consumable material tank of an electric cigarette, as well as a method for filling a consumable material tank of an electric cigarette.

Electric cigarettes are available as disposable products, which are disposed of after consumption of the consumable material, the so-called liquid, or as reusable products, in the case of which the consumable material can be refilled in a tank. It is well known that the refilling of an electric cigarette with consumable material occurs in that the housing of the cigarette needs to be unscrewed in order to get to the consumable material tank. The consumable material is then drizzled into the side of the cigarette housing, which is thus open, by means of a pipette or comparable devices. Such a refilling process proves to not be very comfortable for the user, because it requires skill and precision of the user. It is furthermore possible that consumable material is spilled or is drizzled next to the opening and comes into contact with the skin of the user. Due to the fact that the consumable material usually includes nicotine, which should not come into contact with the human skin in such concentrated form, there is a certain health risk.

In the case of the conventional filling process, it is furthermore possible that consumable material reaches (is drizzled) into areas inside the cigarette, into which it should not reach under any circumstances. This is so, because a misdirected consumable material can wind up in mouth and lung of a user unevaporated, thus in liquid form, when using the electric cigarette for the first time after the refilling. There is a large health risk especially here, because the consumable material comprising a high nicotine concentration should not end up on the mucous membranes of a smoker.

If an electric cigarette or a small conventional bottle comprising a consumable material should end up in the hands of children, there is a health risk in particular for the child. This is so, because consumable material can escape without any problem and can end up on or in the child's body as a result of unscrewing the consumable material bottle or as a result of unscrewing the electric cigarette.

It is an object of the present invention to provide a device for filling an electric cigarette, a consumable material tank of an electric cigarette, as well as a method for filling a consumable material tank of an electric cigarette, wherein the filling process can be carried out in a leakage-free and/or child-proof manner.

Advantageous further developments are the subject matter of the subclaims.

The device has a first tank as storage chamber for accommodating a consumable material and a second tank as storage chamber for accommodating an equalizing fluid, in particular air. The volumes of the tanks can be changed in the opposite direction by means of a control device. This means that the volume of the one tank can be increased by means of the control device and that the volume of the other tank is decreased at the same time. By providing a first and a second connection, wherein these are in each case connected to one of the tanks, the device can be connected to an electric cigarette, which is to be filled. With the embodiment according to the invention, it is possible to introduce the fluid contained in the first tank into the electric cigarette, and to simultaneously extract the air volume, which is displaced by the introduced consumable material, from the electric cigarette by means of the control device. The filling process of an electric cigarette is simplified through this and can be carried out in a leakage-free manner, because it is prevented that the consumable material escapes at an unwanted location as a result of filling-related overpressure in the consumable material tank of the electric cigarette. There is no risk that consumable material is released into the open and ends up on skin or mucous membranes of a user.

By preferably providing two separate cylinders for forming the first and the second tank, the sealing problem can be solved particularly easily.

By preferably providing a toothed rod or a different rod comprising tooth-like engagement elements and a control device comprising a toothed wheel section, a lower development effort furthermore results for embodying the idea of the invention.

By preferably embodying the device in such a way that the volume changes $\Delta V_1$, $\Delta V_2$ of the two cylinders are not equal, a configuration can be attained, in which a larger air volume is extracted from the electric cigarette during the filling process, than consumable material is introduced into the device. It is attained through this that the introduced consumable material does not reach an area inside the electric cigarette under any circumstances, in which area there is the risk that the consumable material ends up in mouth and lung of the smoker, past the vaporizer, when using the electric cigarette for the first time after the refilling by means of a low pressure created in the electric cigarette. This is so, because before the consumable material would end up in such areas of the cigarette, it is sucked back into the device again as a result of the unequal $\Delta V$, before it can propagate inside the electric cigarette.

By preferably providing one cannula each on the first and on the second connection, a cost-efficient embodiment can be attained. This is so, because cannulas, for example of a diameter of 1 mm, are widespread for the medical use, among others, and can be obtained in a cost-efficient manner.

By preferably providing a child-proof lock, it is possible that the control device can only be operated when the entire device (for filling an electric cigarette) is also connected to such an electric cigarette. It is ensured through this that the control device cannot be operated when the device for filling the electric cigarette is not located in a connected position on such a cigarette. If no child-proof lock is provided, consumable material could be ejected from the device at any time by operating the control device and could end up in the hands of children.

To seal the consumable material tank, each of the connections preferably has at least one membrane or a spout valve or a ball valve. The use of a membrane is a particularly cost-efficient solution thereby. When using a spout valve, there is the advantage that excess consumable material, which is present on the cannula as drops, is wiped into the consumable material tank when the cannula is pulled out of the spout valve. The risk of escaping consumable material is reduced through this.

A plurality of exemplary embodiments of the invention will be described below by means of the figures. The following description does not represent a limitation of the invention to the mentioned exemplary embodiments. It is obvious for the person of skill in the art that further exemplary embodiments, which for example combine individual or a plurality of features of the exemplary embodiments specified below, or which even forge completely different implementation paths, are possible within the scope of protection defined by the claims.

FIG. 1a shows a sectional view of an exemplary embodiment of the device 1 comprising two separate cylinders 111, 121, wherein pistons 112, 122 are connected by means of a toothed rod 161.

Figure 2:
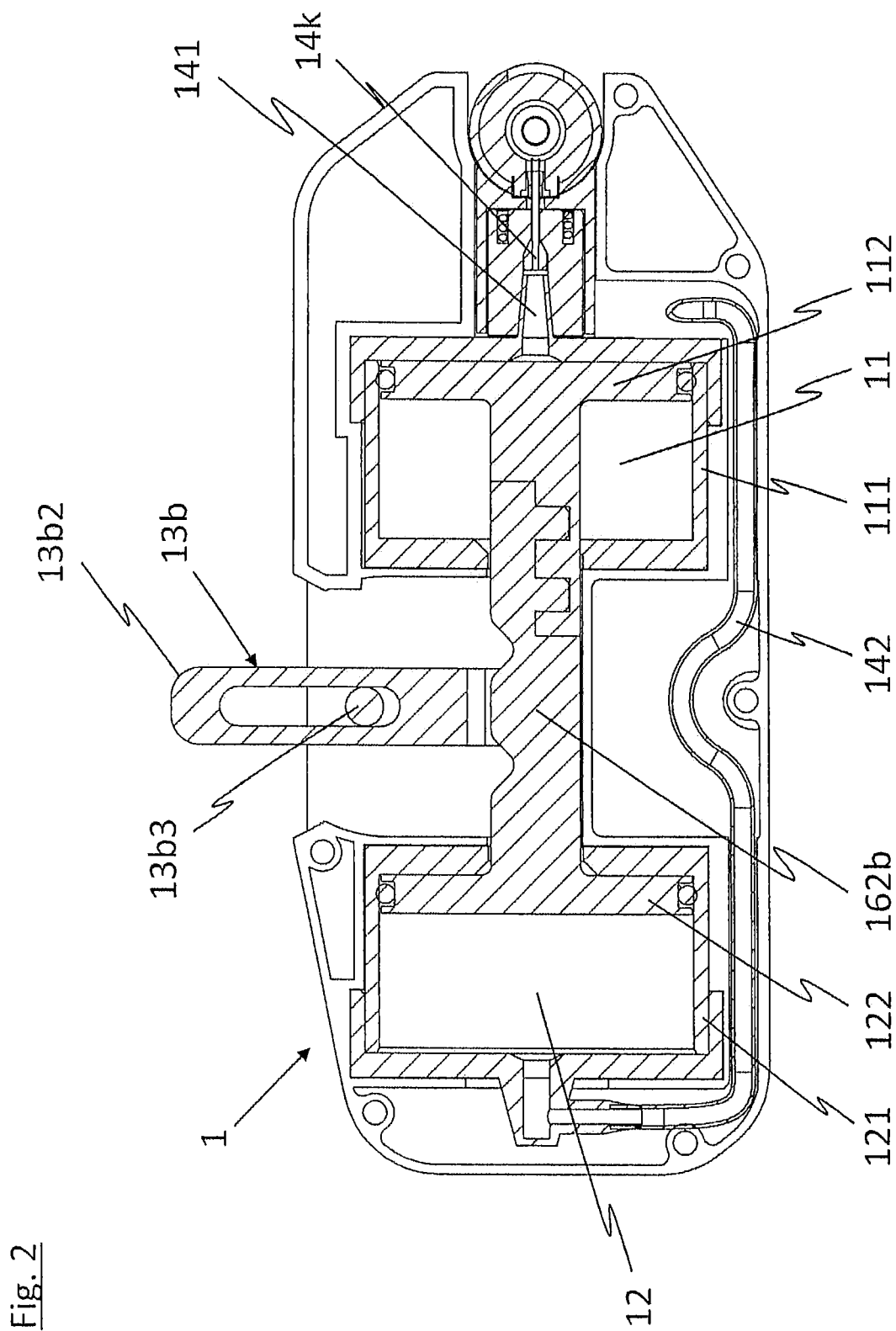

FIG. 2 shows a sectional view of an exemplary embodiment of the device 1 comprising two separate cylinders 111, 121, wherein the pistons 112, 122 are connected by means of a rod 162b, which is coupled to a lever 13b2.

FIG. 3a shows a sectional view of an exemplary embodiment of the device 1 comprising two separate cylinders 111, 121, wherein a control device 13c is embodied integrally with a threaded rod 162c.

Figure 3B:
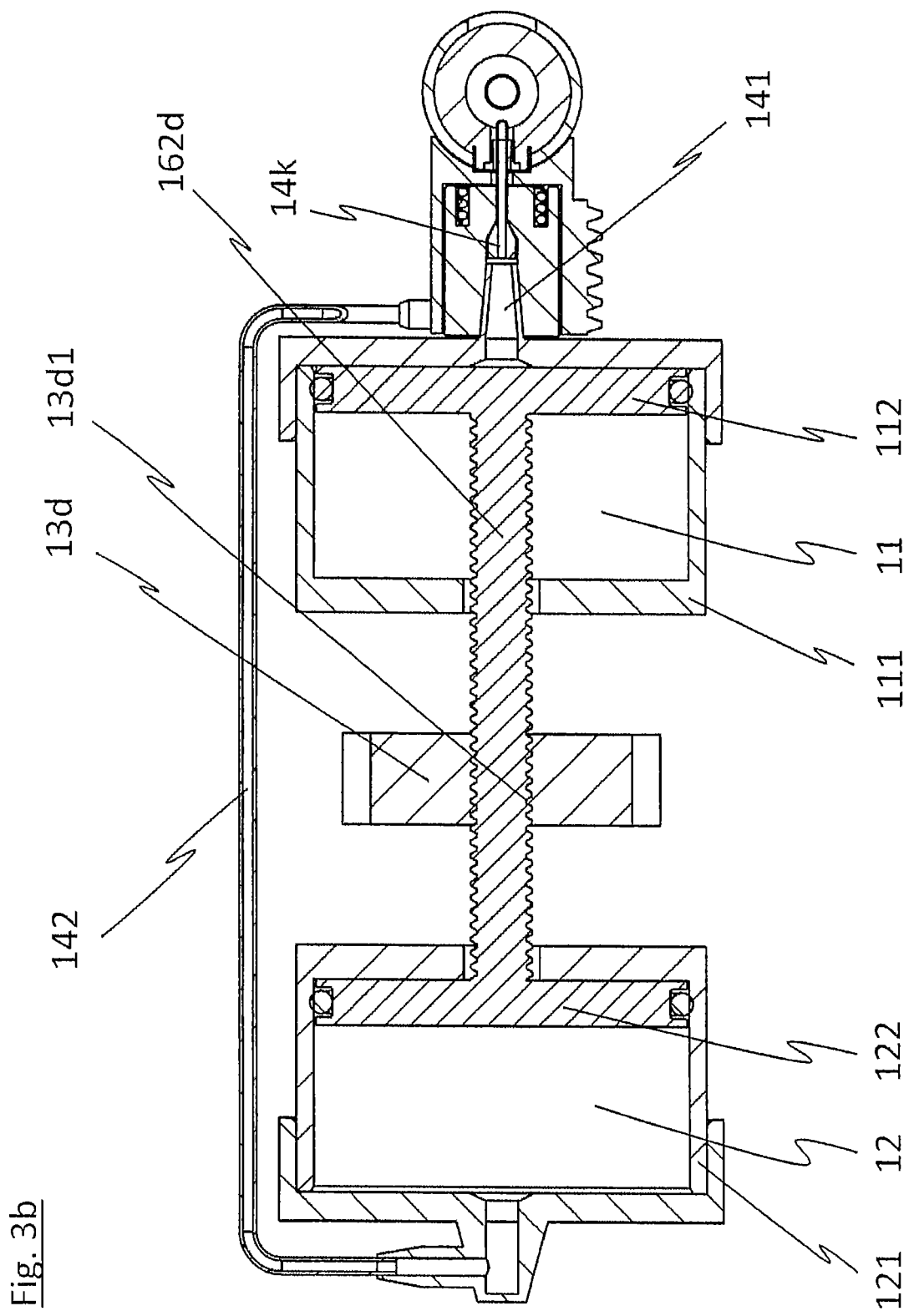

FIG. 3b shows a sectional view of an exemplary embodiment of the device 1 comprising two separate cylinders 111, 121, wherein two pistons 112, 122 are embodied integrally with a threaded rod 162d.

Figure 4A:
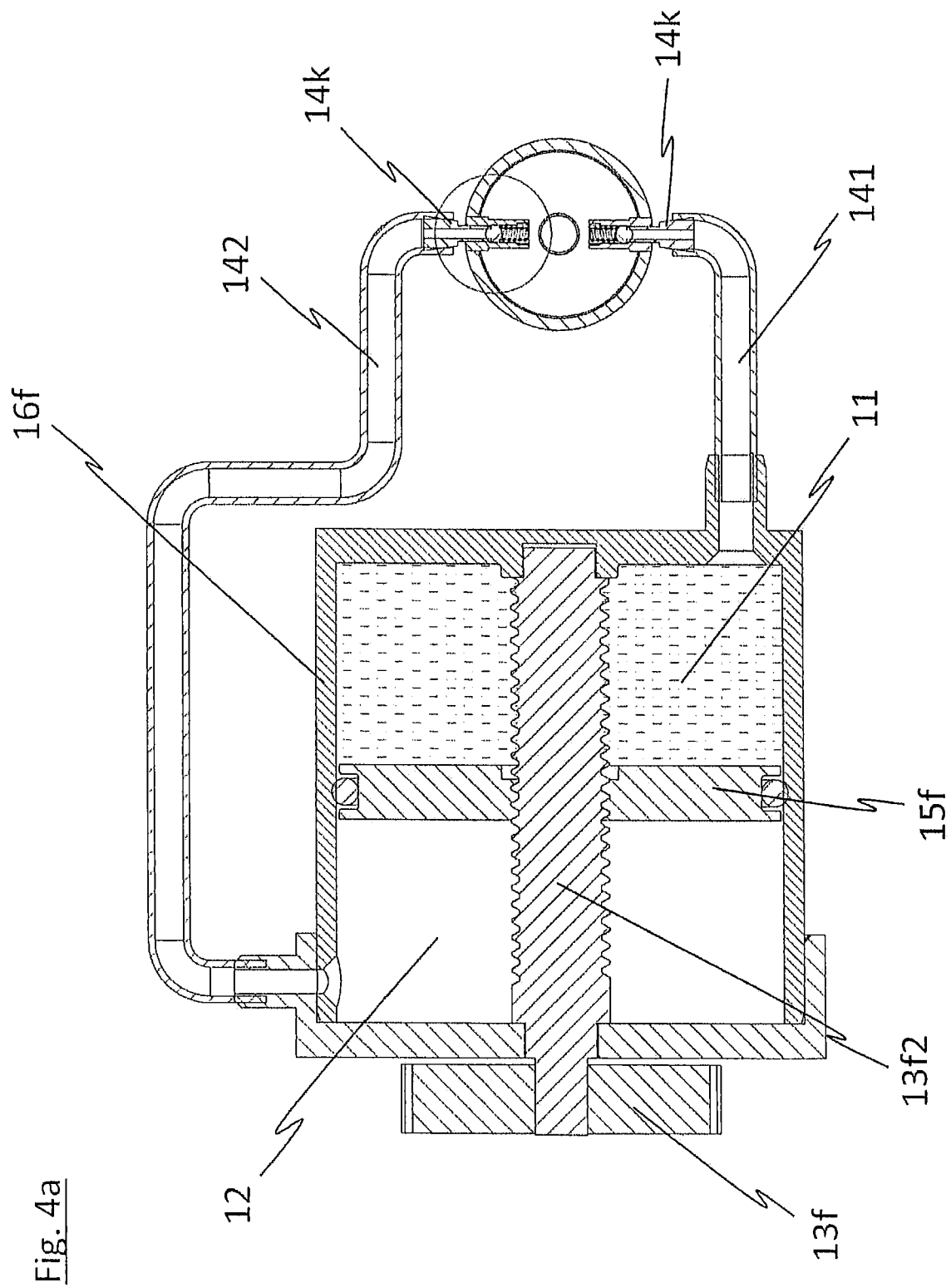

FIG. 4a shows an exemplary embodiment of the device 1 comprising a joint cylinder 16f for both tanks 11, 12, wherein a joint piston 15f can be moved back and forth on a threaded rod 13f2.

Figure 4B:
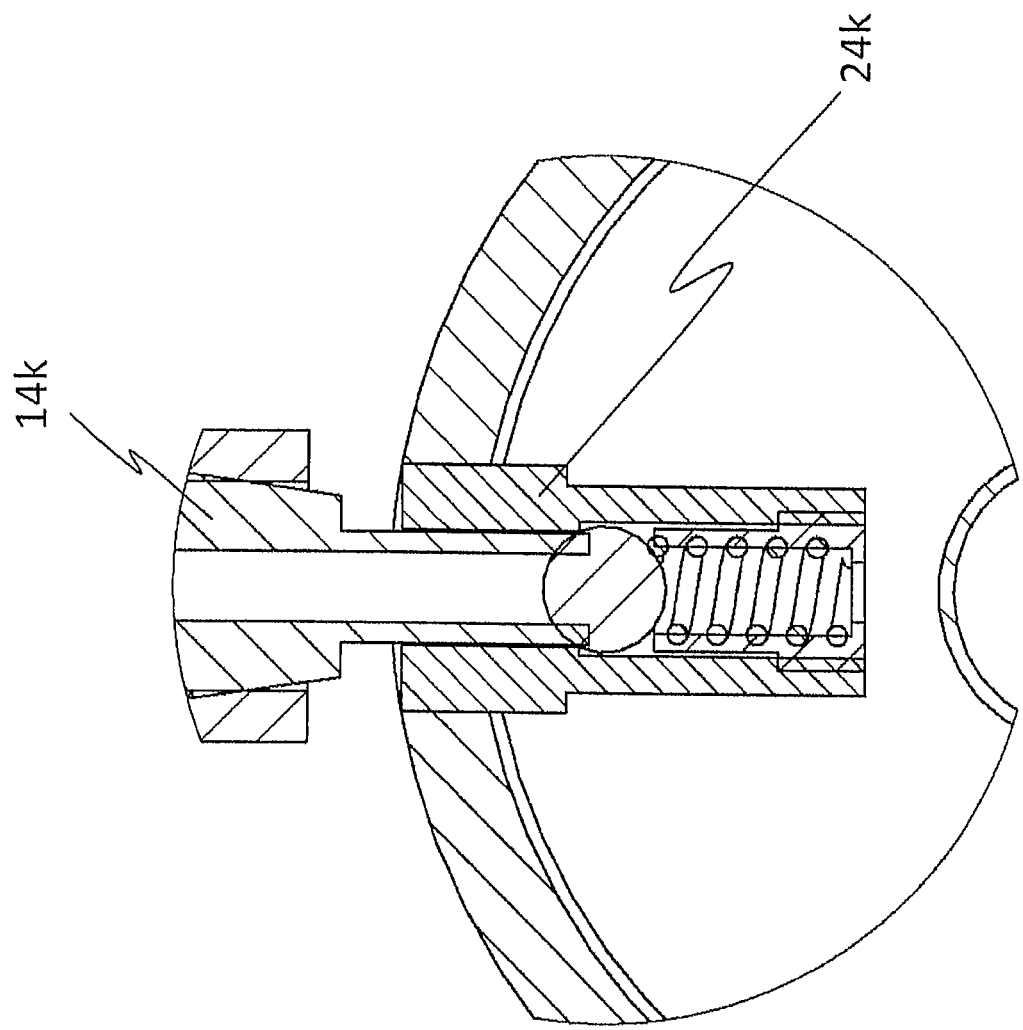

FIG. 4b shows an enlarged section from FIG. 4a, in which the engagement of a cannula 14k with a ball valve 24k of a consumable material tank 2 is illustrated.

Figure 5A:
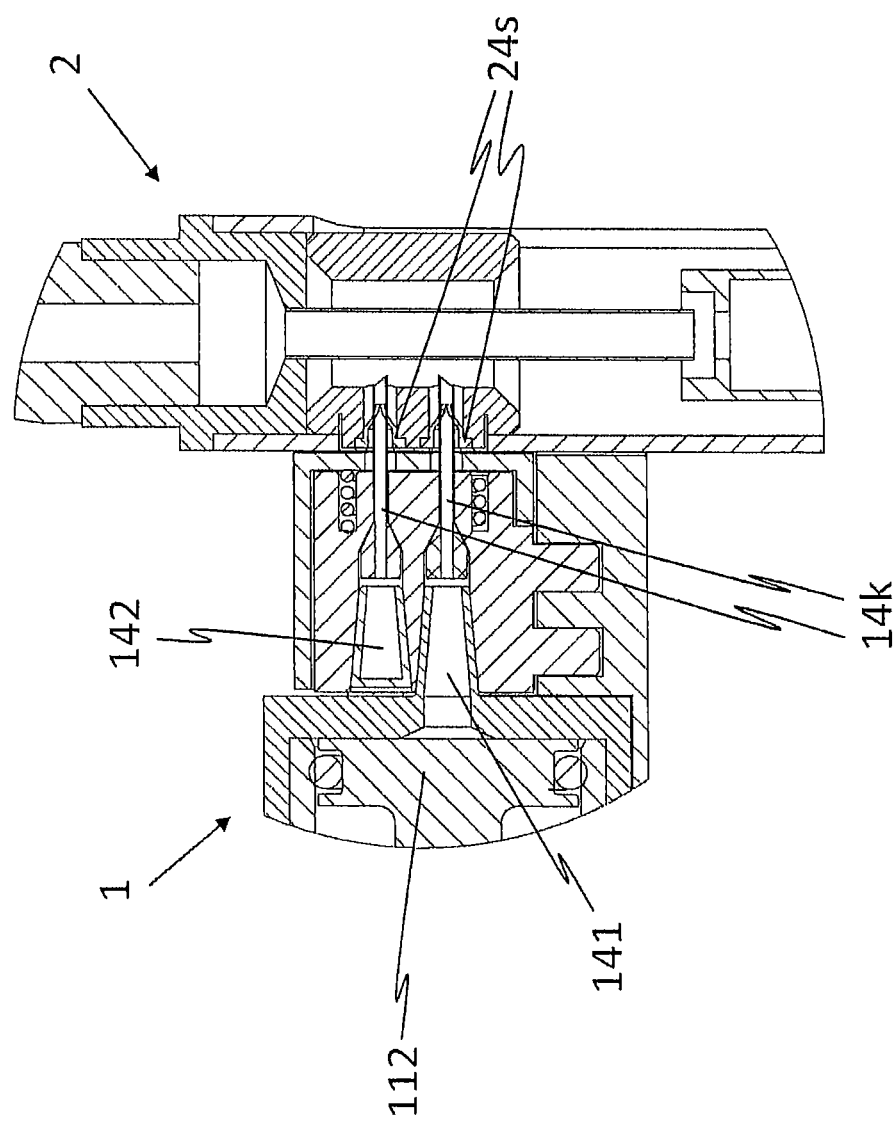

FIG. 5a shows a detailed view of an exemplary embodiment of device 1 and consumable material tank 2, which has spout valves 24s.

Figure 5B:
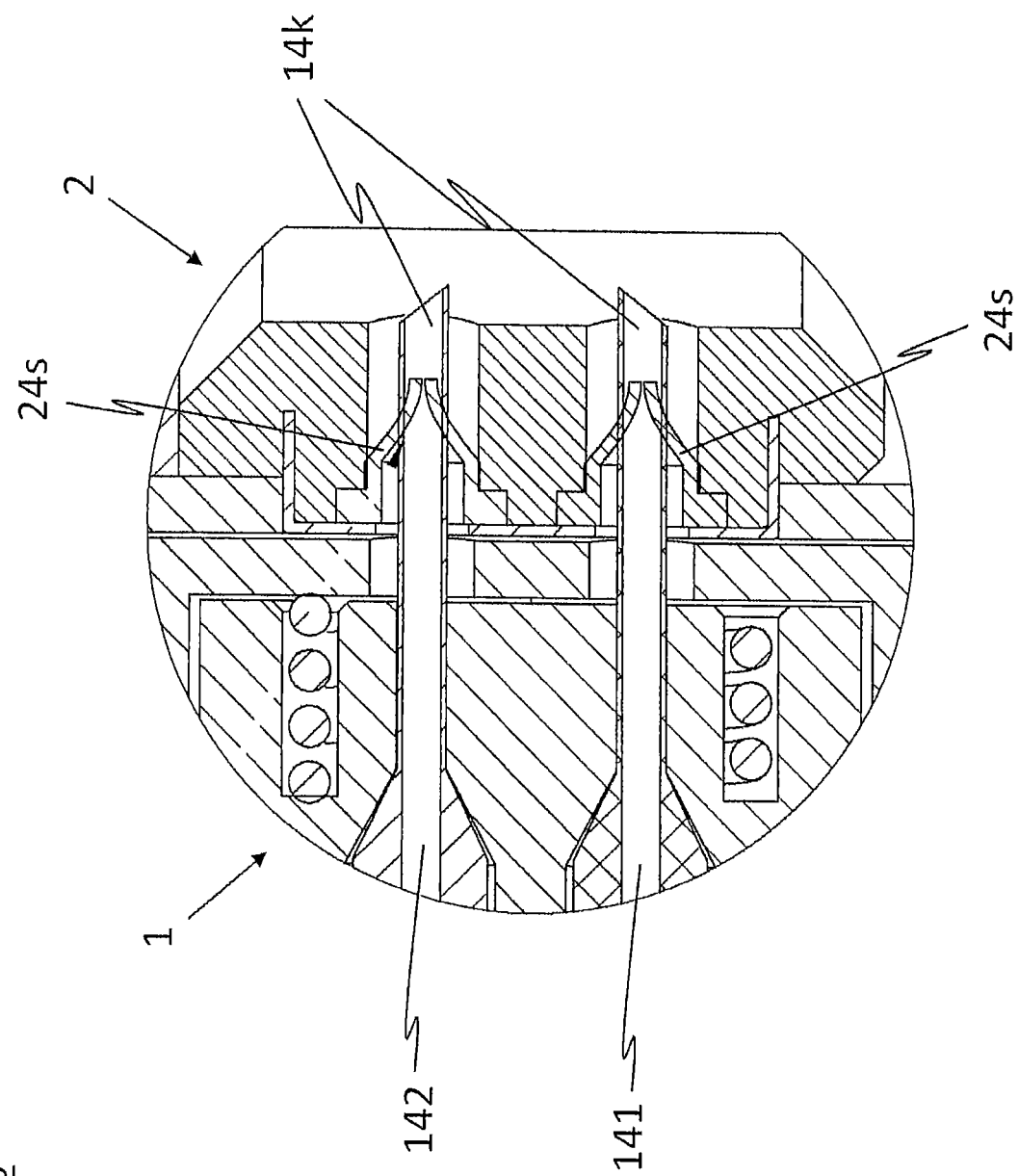

FIG. 5b shows a detailed view of the illustration from FIG. 5a.

Figure 6A:
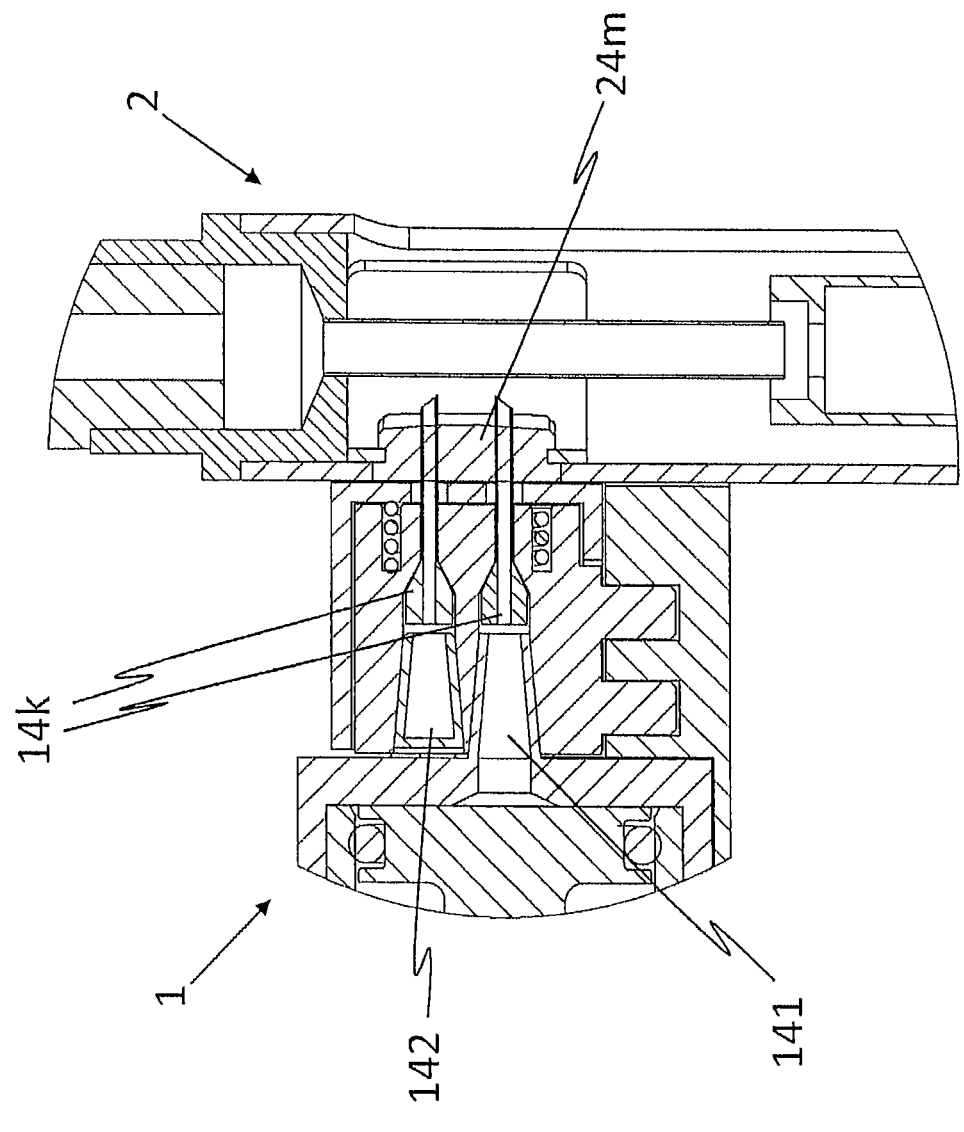

FIG. 6a shows a detailed view of an exemplary embodiment of device 1 and consumable material tank 2, which has a membrane 24m.

Figure 6B:
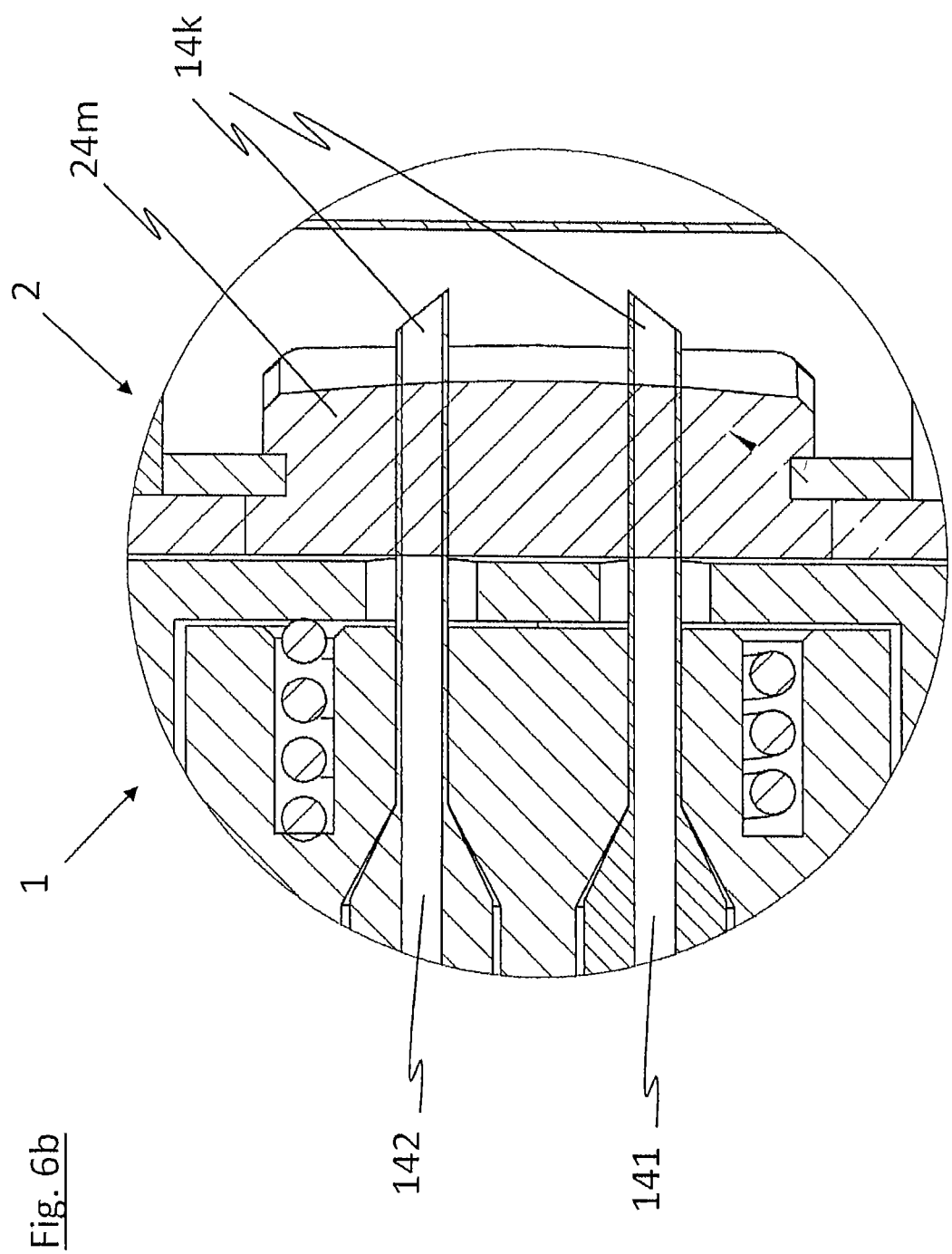

FIG. 6b shows a detailed view of the illustration from FIG. 6a.

Figure 7A:
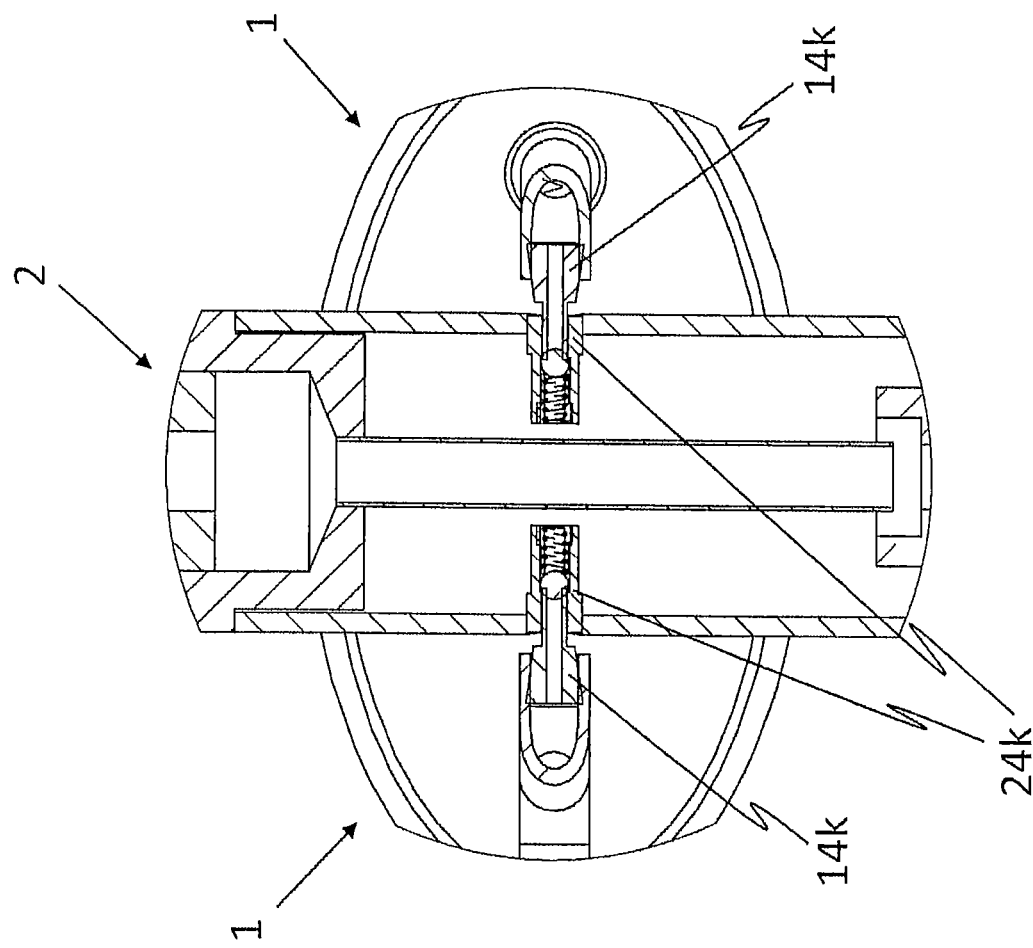

FIG. 7a shows a detailed view of the exemplary embodiment from FIG. 4a, viewed from the right.

Figure 7B:
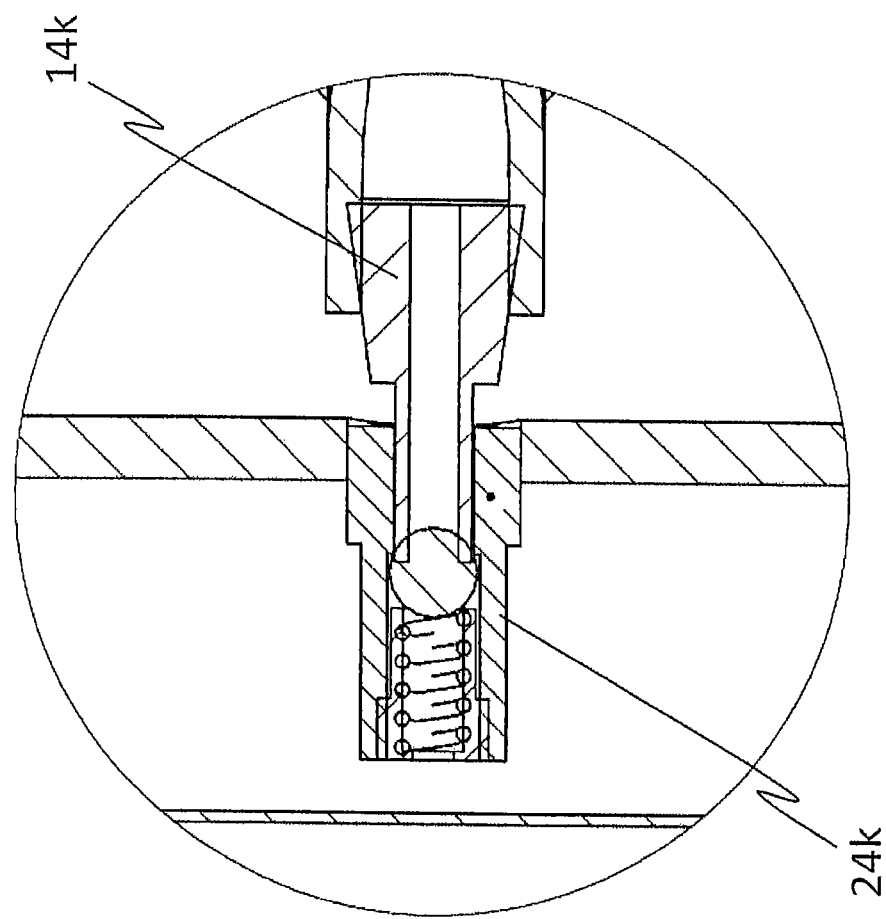

FIG. 7b shows a detailed view of the illustration from FIG. 7a.

FIG. 8 shows different exemplary embodiments of the device 1, connected to an electric cigarette.

Figure 9:
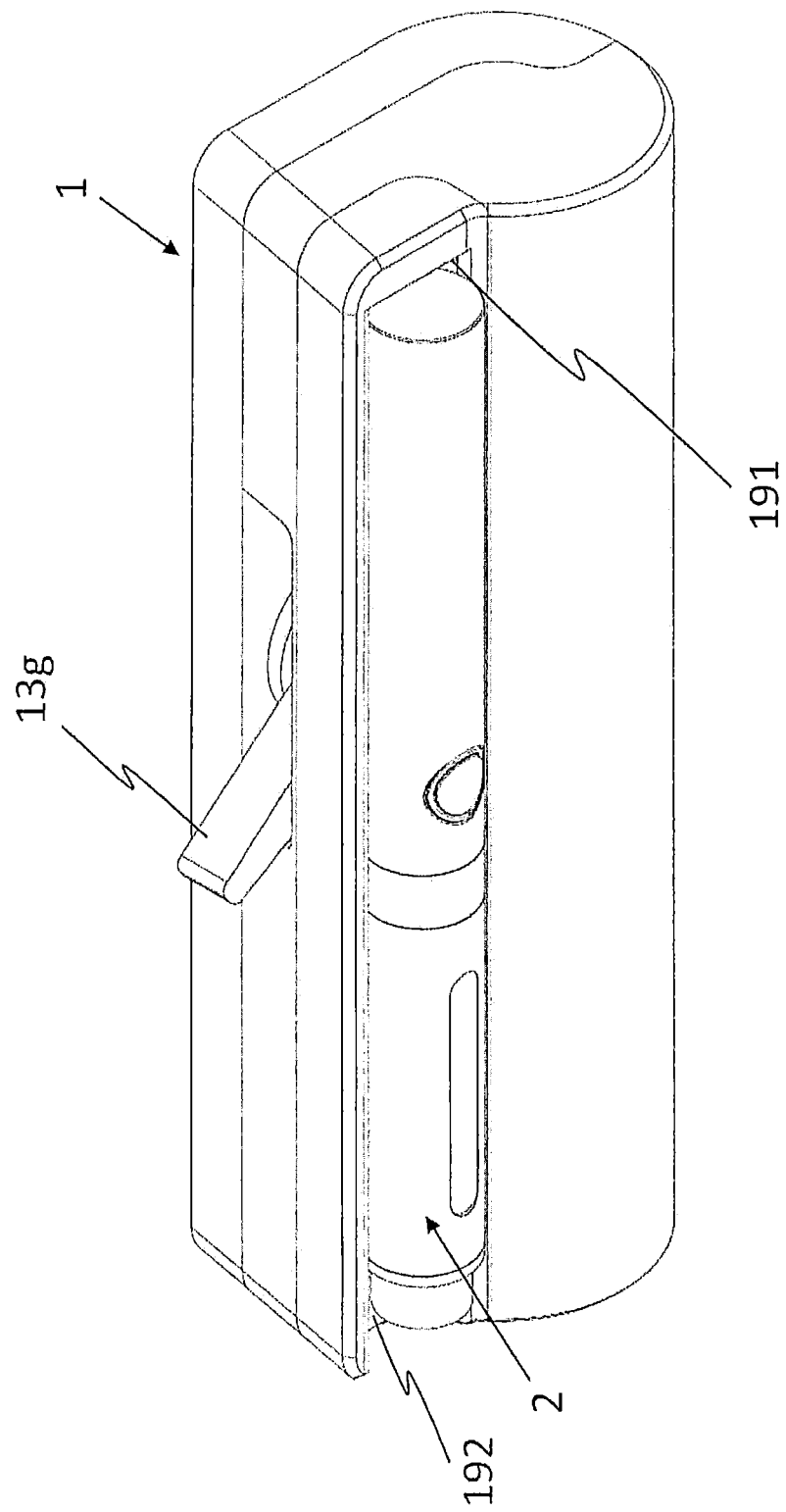

FIG. 9 shows an alternative exemplary embodiment of the device 1 comprising an alternative connecting concept between device 1 and consumable material tank 2.

Figure 10:
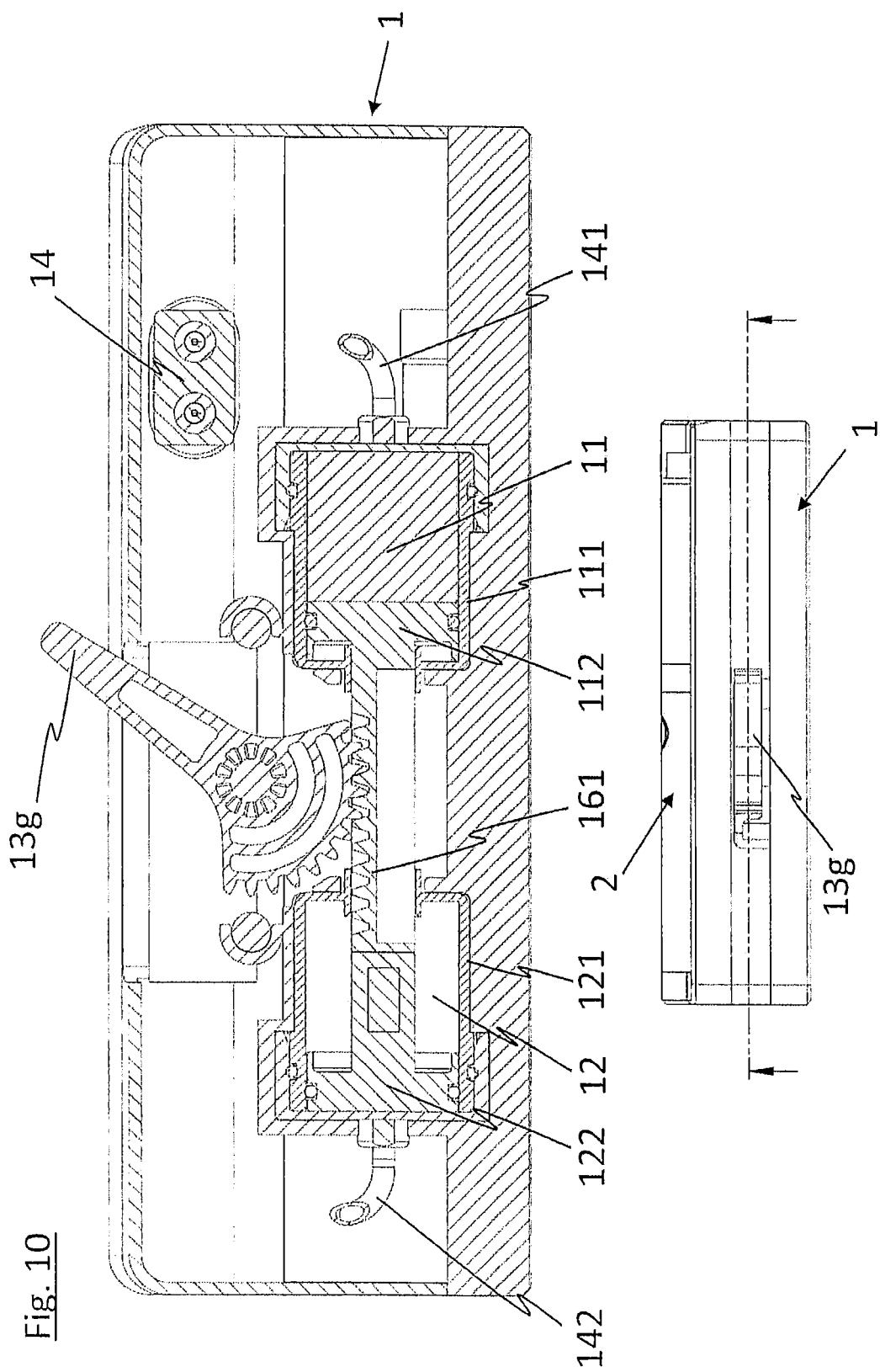

FIG. 10 shows the exemplary embodiment from FIG. 9 in a cut view.

Figure 11:
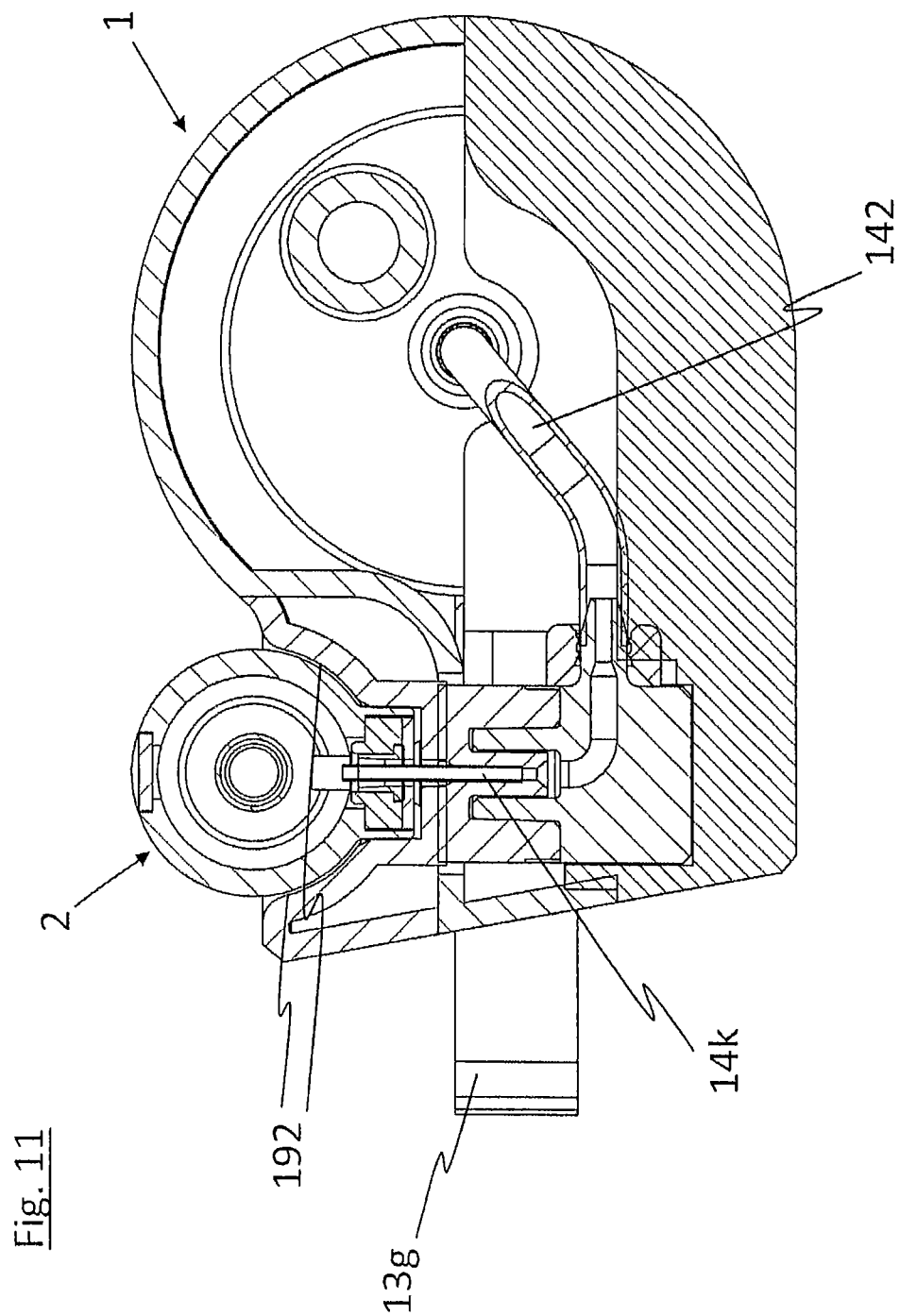

FIG. 11 shows a further sectional view of the exemplary embodiment from FIG. 9.

Figure 12:
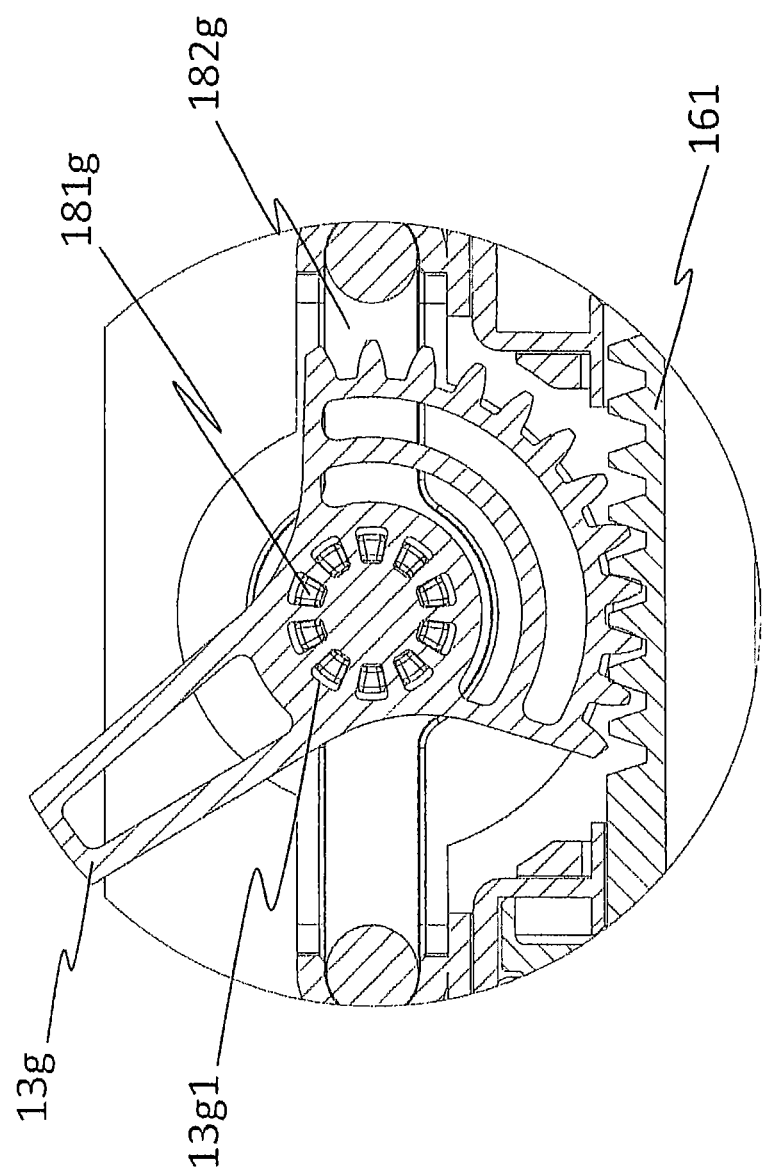

FIG. 12 shows a detailed view of the child-proof lock 18 of the exemplary embodiment from FIG. 9.

Figure 13:
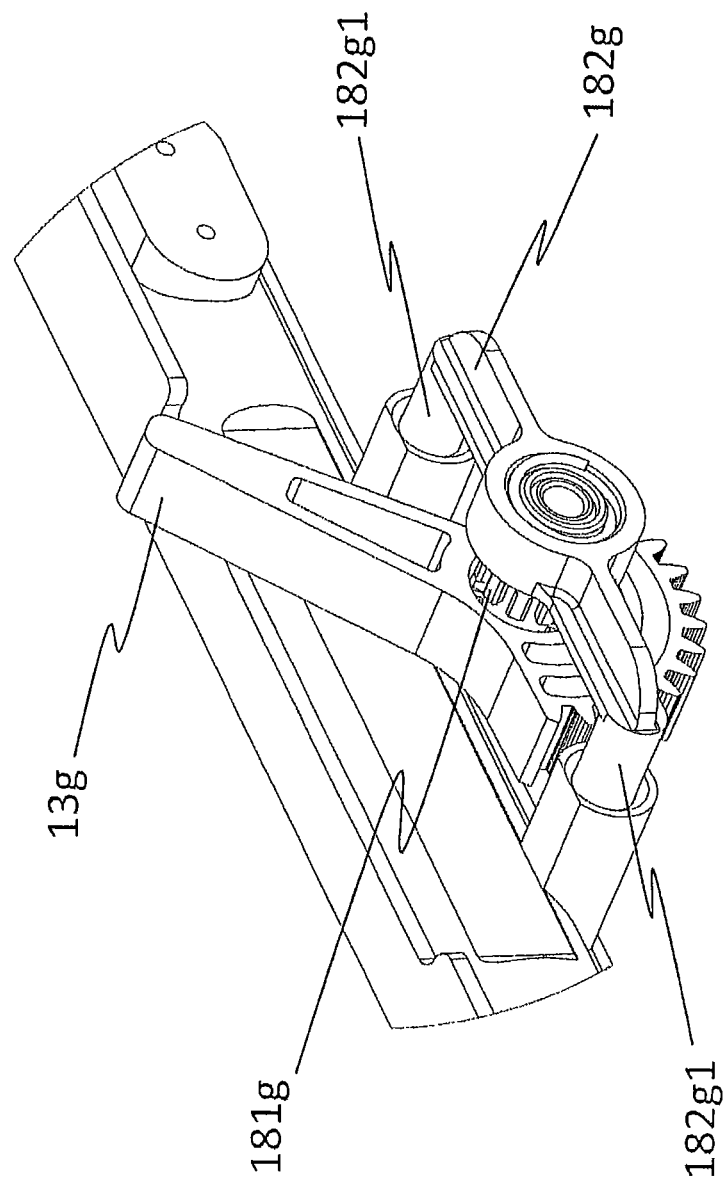

FIG. 13 shows an isometric detailed view of the child-proof lock 18 of the exemplary embodiment from FIG. 9.

Figure 1A:
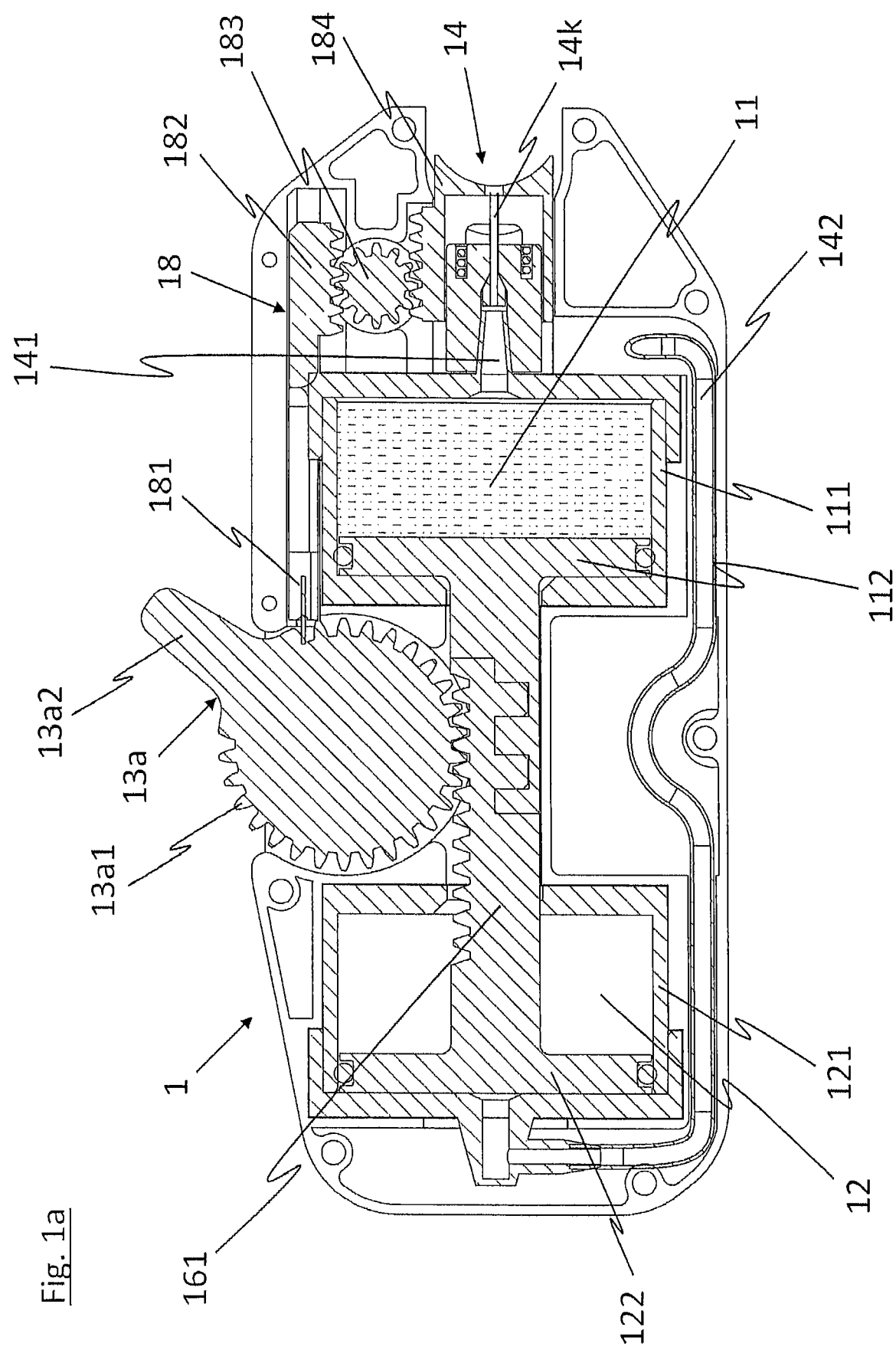
FIG. 1b shows a detailed view of the exemplary embodiment from FIG. 1a, wherein the control device 13a is blocked by means of the child-proof lock 18.
FIG. 1c shows a detailed view of the exemplary embodiment from FIG. 1a, wherein the control device 13a is released by means of the child-proof lock 18.

The exemplary embodiment of the device 1 illustrated in FIG. 1a has a first storage chamber in the form of a first tank 11 for accommodating a consumable material and a second storage chamber in the form of a second tank 12 for accommodating air or another equalizing fluid. The first tank 11 has a first cylinder 111 as hollow cylinder and a first piston 112. As seal between piston 112 and cylinder 111, an annular seal is attached between cylinder jacket and piston circumference. The second tank 12 has a second cylinder 121 as hollow cylinder and a second piston 122, which are sealed analogous to the first tank 11. The first tank 11 is fluidically connected to the first connection 141. The second tank 12 is fluidically connected to a second connection 142. The pistons 112, 122 are connected to one another by means of a toothed rod 161, wherein the toothed rod 161 in the exemplary embodiment is embodied in two pieces for an easier installation, and each of the pieces forms a unit in each case comprising one piston 112, 122. A control device 13a engages with the toothed rod 161 with a toothed wheel section 13a1. The control device 13a furthermore has a lever 13a2. In the illustration shown in FIG. 1a, the lever 13a2 of the control device 13a is moved to the right. By moving the lever from the illustrated position to the left, the unit of threaded rod 161, first piston 112 and second piston 122 would be moved to the right, based on the Figure. The consumable material contained in the first tank 11 is thereby pushed through the first channel 141, through the cannula 14k. Air is simultaneously sucked through the second piston 122 from the second connection 142 (through a further cannula 14k, which cannot be seen in the illustration), into the second tank 12. As can be seen in FIG. 1a, the first channel 141 is fluidically connected to a cannula 14k. The second channel 142 is fluidically connected to a second cannula 14k, which cannot be seen in the shown illustration, because it is located behind the image plane.

A child-proof lock 18, which has a bolt 181, a first carriage 182, a toothed wheel 183, as well as a second carriage 184, is furthermore illustrated in FIG. 1a. In the illustration shown in FIG. 1a, the second carriage 184 is arranged in such a way that the cannulas 14k are located inside the second carriage 184. The first carriage 182 and the second carriage 184 are arranged so that they can be shifted horizontally, wherein even though the toothed wheel 183 is axially secured, it is rotatable. The bolt 181 is fixedly connected to the first carriage 182. The first carriage 182 and the second carriage 184 in each case have a toothed section and engage with the toothed wheel 183. The bolt 181 furthermore engages with the toothed wheel section 13a1 of the control device 13a and blocks it. When the second carriage 184 is moved to the left by means of an external force application, a rotation of the toothed wheel 183 is caused in the clockwise direction, by means of which the first carriage 182 and the bolt 181, in turn, are moved to the right. The bolt 181 is thereby moved out of the toothed wheel section 13a1 of the control device 13a, and the cannulas 13k are no longer covered by the second carriage 184, the cannula tips are then in fact located outside of the second carriage 184. The second carriage 184 thereby moves back behind the cannula tips and releases them.

Figure 1B:
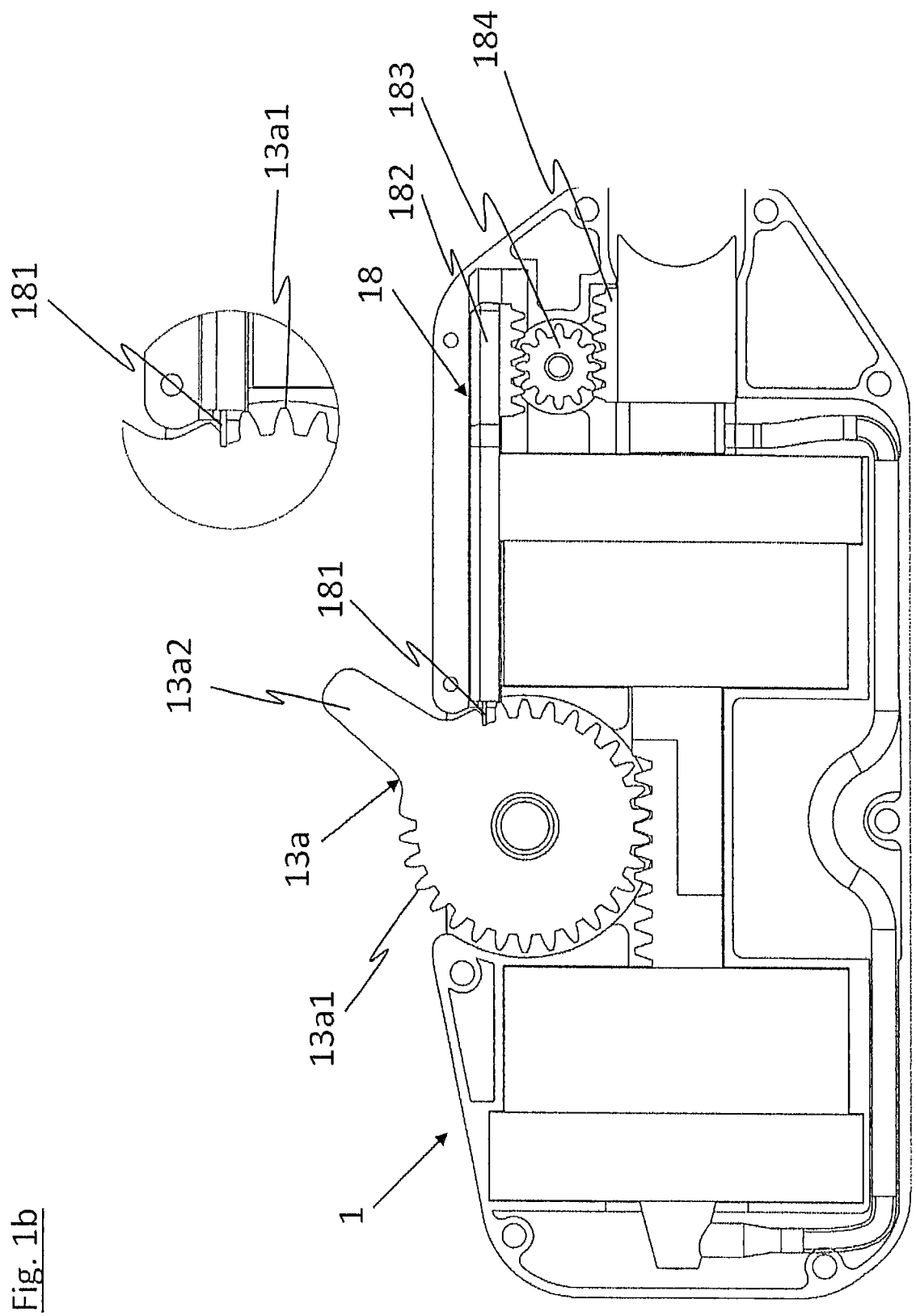

In the illustration shown in FIG. 1b, the child-proof lock 18, more precisely the bolt 181, is in a locked position. In this locked position, the bolt 181 engages with the toothed wheel section 13a1 of the control element 13a. The control element 13a is thus blocked. A movement or a rotation, respectively, of the control device 13a by means of a force application on the lever 13a2 is not possible in this state. In this state of the child-proof lock 18, it is thus not possible to eject consumable materials from the first tank 11.

FIG. 1c shows the exemplary embodiment from FIGS. 1a and 1b, wherein the child-proof lock 18, however, is in a non-locked state, thus in a released state. As a result of an external force application on the second carriage 184, the latter was shifted to the left, whereby the toothed wheel 183 was rotated in clockwise direction, whereby the first carriage 182 was pushed to the right and has thus moved the bolt 181 out of the toothed wheel section 13a1 of the control device 13a. In the illustration shown in FIG. 1c, the control device 13a is thus not blocked by the child-proof lock 18. A movement of the threaded rod 161 and thus of the pistons 112 and 122 from left to right is possible by means of a force application on the lever 13*a*2, whereby consumable materials are ejected, and air is sucked in, in each case through one of the cannulas 14*k*.

FIG. 2 shows an exemplary embodiment of the device 1 without child-proof lock 18, wherein the control device 13*b* is not embodied as toothed wheel, as in the previous exemplary embodiments, but as lever 13*b*2 comprising a center of rotation 13*b*3 on the pivotal point of the lever. A non-illustrated joint acts between a rod 162*b* and the control device 13*b*. The center of rotation 13*b*3 is fixedly arranged on the housing of the device 1. By moving the upper end of the lever 13*b*2 from left to right, a shifting of the rod 162*b* from right to left results due to the center of rotation 13*b*3. The control device 13*b* also has an elongated hole, with which the center of rotation 13*b*3 engages. The elongated hole allows that the distance from the above-mentioned non-illustrated joint to the center of rotation 13*b*3 changes in response to a movement of the lever 13*b*2. The remaining components are to be understood analogous to the shown exemplary embodiment from FIGS. 1*a*, 1*b* and 1*c*.

The exemplary embodiment shown in FIG. 3*a* has a first tank 11 for accommodating a consumable material and a second tank 12 for accommodating air or another equalizing fluid. The first tank 11 has a first cylinder 111 and a first piston 112. The second tank 12 has a second cylinder 121 and a second piston 122, analogous to the previously introduced exemplary embodiments. The control device 13*c*, however, has a hand wheel. The control device 13*c* is connected integrally to a threaded rod 162*c*.

In a modification of this exemplary embodiment, the control device 13*c* is connected to the threaded rod 162*c* in a rotatably fixed manner, but it is not embodied integrally therewith.

By rotating the control device 13*c* around an axis, which runs horizontally in the image plane, the threaded rod 162*c* is also rotated due to integral design or due to the rotationally fixed connection between control device 13*c* and threaded rod 162*c*. The first piston 112 as well as the second piston 122 in each case have an internal thread. These internal threads are threadedly engaged with the threaded rod 162*c*. When the threaded rod 162*c* is rotated by means of the control device 13*c*, the pistons 112, 122 are shifted to the left and right on the threaded rod, depending on the direction of rotation. The pistons 112, 122 are thereby prevented from rotating along with the threaded rod 162 due to the friction between annular seal, pistons 112, 122 and cylinder 111, 121. In a non-illustrated exemplary embodiment, the pistons 112, 122 in the cylinders 111, 121 are guided by means of spring and groove in order to prevent a rotating of the pistons 112, 122 together with the threaded rod 162*c*. All remaining elements are to be understood analogous to the previously introduced exemplary embodiments.

The exemplary embodiment shown in FIG. 3*b* shows a modification of the exemplary embodiment shown in FIG. 3*a*, but the threaded rod 162*d* in the shown exemplary embodiment is not fixedly connected to the control device 13*d* or is embodied integrally therewith. In fact, the first piston 112 and the second piston 122 are fixedly connected to the threaded rod 162*d*. The control device 13*d* has an internal thread 13*d*1, which is threadedly engaged with the threaded rod 162*d*. The control device 13*d* is furthermore held axially by means of non-illustrated flanks of the housing of the device 1, so as to prevent the control device 13*d* from moving to the left and right. By rotating the control element 13*d*, the threaded rod 162*d* can thus be shifted to the left and right in the image plane, together with the pistons 112, 122. All remaining elements are to be understood analogous to the previously introduced exemplary embodiments.

The exemplary embodiment of the device 1 illustrated in FIG. 4*a* has joint cylinder 16*f* for the first tank 11 and the second tank 12. The two tanks 11, 12 are separated from one another by means of a joint piston 15*f*. The piston 15*f* has an internal thread, which is threadedly engaged with a threaded rod 13*f*2. A control device 13*f* is fixedly connected to the threaded rod 13*f*2. In a modification of the exemplary embodiment, threaded rod 13*f*2 and control device 13*f* are embodied integrally.

If the control device 13*f* is rotated about an axis, which runs horizontally in the image plane, together with the threaded rod 13*f*2, the piston 15*f*, which is in threadedly engaged with the threaded rod 13*f*2, is shifted to the left or right. In response to a movement of the piston 15*f* to the right, consumable material is conveyed from the tank 11 through the first connection 141, whereby air is sucked from the second connection 142 into the second tank 12. Analogous to the previous exemplary embodiments, a rotation of the piston 15*f* together with the threaded rod 13*f*2 is prevented in response to the rotation on the control device 13*f*.

FIG. 4*b* shows the engagement of a cannula 14*k* of the device 1 with a ball valve 24*k* of a consumable material tank 2.

FIG. 5*a* shows the engagement of two cannulas 14*k* of the device 1 with two spout valves 24*s* of the consumable material tank 2. The lower cannula 14*k* is fluidically connected to the first connection 141, which is fluidically connected to the first tank 11, in turn. The upper cannula 14*k* is fluidically connected to the second connection 142, which is fluidically connected to the second tank 12, in turn. The illustration in FIG. 5*a* shows the engagement of the device 1 with a consumable material tank 2 of an electric cigarette after the filling process of the electric cigarette has been concluded. The piston 112 of the first tank 11 is located in a position, which has been moved completely to the right, in which the entire content of the first tank 11 has already been conveyed through the first channel 141 and through the lower cannula 14*k* into the consumable material tank 2 of the electric cigarette. The consumable material tank 2 is sealed by means of an upper and a lower spout valve 14*s*. The arrangement of the cannulas 14*k* and of the spout valves 24*s* in the configuration "fill on the bottom, extract on the top" serves the purpose that consumable material is supplied into the consumable material tank 2 in a lower area and that a displaced air volume is extracted in an upper area. Due to the difference in density of consumable material and air, a different arrangement would not make any sense, because the consumable material, which is filled in, would otherwise be extracted directly again.

FIG. 5*b* shows a detailed view of the illustration from FIG. 5*a*. The spouts of the spout valves 24*s* are illustrated schematically so as to overlap with the cannulas 14*k* in this illustration. After the penetration of the cannulas, the spouts abut against the outer jackets of the cannulas 14*k*. The schematic illustration of the spouts shows a closed state.

FIG. 6*a* shows the exemplary embodiment from FIG. 5*a*, wherein a membrane 24*m* is provided instead of the spout valves 24*s* for sealing the consumable material tank 2. This membrane 24*m* can be provided as rubber-elastic component, which is pierced by means of the cannulas 14*k*. By pulling out the cannulas 14*k* after the filling of the consumable material tank 2, the openings, which are inserted into the membrane 24m, contract again and seal the consumable material tank 2. The membrane 24m is provided as disposable product, which can be used several times, which can be replaced, when the sealing effect no longer exists.

FIG. 6b shows a detailed view of the illustration from FIG. 6a. The shading of the membrane 24m can be seen therein inside the cannulas 14k. This illustration corresponds to a state, in which the membrane 24m has been pierced directly by means of the cannulas 14k. As soon as a fluid exchange (filling and extraction process) occurs, the membrane pieces, which were punched out, move out of the cannulas 14k.

FIG. 7a shows the exemplary embodiment of the device 1, which is illustrated in FIG. 4a and which is in a state, in which it is connected to the consumable material tank 2. In the shown illustration, the consumable material tank 2 is contacted from different sides, from the left and right. One cannula 14k of the device 1 and a ball valve 24k of the consumable material tank 2 are in each case illustrated on the left and on the right side.

FIG. 7b shows a detailed view of the illustration from FIG. 7a. The cooperation of cannula 14k of the device 1 and ball valve 24k of the consumable material tank 2 can be seen.

FIG. 8 shows isometric views of different embodiments of the device 1, while they are connected to a consumable material tank 2 of an electric cigarette. The exemplary embodiment from FIG. 4a is illustrated on the very left, the exemplary embodiments from FIG. 3a and FIG. 3b are illustrated in the middle, wherein the exemplary embodiment from FIG. 2 is illustrated on the right side.

FIG. 9 shows an isometric view of an alternative connecting concept between device 1 and electric cigarette or consumable material tank 2, respectively, In the case of the previously described exemplary embodiments (see in particular FIG. 8), the device 1 and the electric cigarette to be filled are coupled to one another in a position, in which the main body axes of device 1 and electric cigarette have an angle of approximately 90 degrees. To simplify the coupling process between device 1 and electric cigarette or consumable material tank 2, respectively, the device 1 of this exemplary embodiment has a shell element comprising an accommodation 192 for inserting the electric cigarette. The inner contour of the accommodation 192 corresponds to the outer contour of the electric cigarette, so that the latter can be inserted into the device 1 in a positive manner. The shell element further has an end stop 191 for aligning the electric cigarette in its axial direction inside the device 1. The device 1 has a control device 13g, and the mode of operation is essentially analogous to the mode of operation of the previous exemplary embodiments. In the lower section, FIG. 10 shows a top view onto the illustration from FIG. 9 with a view onto the surface of the device 1, in which the control device 13g is arranged. In this top view, a sectional line is added by means of arrows, which show the folding direction of the section. The section is illustrated in the upper sector of FIG. 10 in an enlarged manner. Analogous to the illustration in FIG. 1a, the first tank 11 and the second tank 12 are shown, wherein each of the tanks 11, 12 has a cylinder 111, 121 as well as a piston 112, 122. The connections 141 and 142, which run outside of the sectional plane to the interface 14, are also illustrated. The pistons 112, 122 are furthermore coupled to one another by means of a toothed rod 161.

FIG. 11 shows a further sectional view of the exemplary embodiment from FIG. 9, cut perpendicular through the main axis of the electric cigarette. The electric cigarette or the consumable material tank 2, respectively, are illustrated in a position, which is coupled to the device 1. The electric cigarette is thereby located inside the accommodation 192 or inside the shell element, respectively.

FIG. 12 shows a cut detailed view of the exemplary embodiment from FIG. 9, by means of which the mode of operation of the child-proof lock 18 is explained. The child-proof lock 18 has a bolt 182g, which has pins 181g, which are arranged on the bolt 182g in a circular manner. The control device 13g also has recesses 13g1, which are arranged in a circular manner and which are arranged in such a way that an engagement of the pins 181g with the recesses 13g1 is possible. When the pins 181g engage with the recesses 13g1, the control device 13g is thus blocked. This blocked state is then maintained by means of spring elements when no electric cigarette is located on the device 1 in a coupled position. For this purpose, a part of the device 1, which forms the accommodation for the electric cigarette, is coupled to the child-proof lock 18 in such a way that the pins 181g are shifted into the drawing plane (away from the observer) by inserting an electric cigarette (into the device 1), and the control device 13g is thus released. The control device 13g can then be moved to fill the consumable material tank 2. By removing the electric cigarette from the device 1 after the filling process of the consumable material tank 2, the pins 181g are moved back in the direction of the observer (of FIG. 12) again by means of spring force, so that the pins 181g engage with the recesses 13g1 again and the control device 13g is thus blocked.

FIG. 13 shows the child-proof lock 18 in a perspective view, in order to clarify the mode of operation thereof. The bolt 182g has two pistons 182g1, which make it possible to guide the bolt 182g in the housing of the device 1. The part of the device 1, which forms the accommodation for the electric cigarette, is furthermore coupled to the piston 182g1 in such a way that the bolt 182g or the pins 181g, respectively, are moved out of the control device 13g, when an electric cigarette is inserted into the device 1. The control device 13g is thus released, as illustrated in FIG. 13. The bolt 182g is pushed (back) into a position, which blocks the control device 13g and in which the pins 181g engage with the control device 13g, by means of a spring, which is not illustrated in this view.

As already explained, modifications of the above-described exemplary embodiments, which do not leave the scope of protection defined by the claims, are obvious to the person of skill in the art. In particular the pistons 112, 122 from the exemplary embodiments of FIGS. 1a, 2 and 10 are thus coupled to the toothed rod 161 in such a way that an integral, fixed connection is present. This coupling, however, needs to neither be embodied integrally nor fixedly. Every fixed or loose, indirect or direct operative connection, which allows transferring forces in a form, so that the intended object of the subject matters of the individual claims can be fulfilled, is to be understood as a coupling in terms of this teaching.

The invention claimed is:
1. A device comprising:
   a first storage chamber configured and arranged for accommodating a consumable material,
   an interface, which is connected to a first connection, which is fluidically connected to the first storage chamber, characterized by
   a second storage chamber configured and arranged for accommodating an equalizing fluid, and
   a control device, wherein
   the device is configured and arranged to fill an electric cigarette wherein the volumes of the first storage cham- ber and of the second storage chamber are changed in an opposite direction by means of the control device, and wherein the interface has a second connection, which is fluidically connected to the second storage chamber, further having a child-proof lock, which is provided with a bolt configured and arranged for blocking and releasing the control device.

2. The device of claim 1, wherein the first storage chamber has a first hollow cylinder and a first piston, and the second storage chamber has a second hollow cylinder and a second piston, and the first piston is configured and arranged to facilitate a first volume change, $\Delta V1$, of the first storage chamber when extended into and retracted out of the first hollow cylinder; and the second piston is configured and arranged to facilitate a second volume change, $\Delta V2$, of the second storage chamber when extended into and retracted out of the second hollow cylinder.

3. The device of claim 2, wherein the control device has a toothed wheel section, the first piston and the second piston are indirectly or directly coupled to one another by means of a control rod in the form of a toothed rod, threaded rod or a different rod comprising tooth-like engagement elements, and the device is constructed in such a way that the toothed wheel section and the control rod engage with one another.

4. The device of claim 2, wherein the control device has a lever, wherein the first piston and the second piston are indirectly or directly coupled to the lever.

5. The device of claim 4, wherein the control device has a center of rotation for the lever, wherein the first piston and the second piston are indirectly or directly coupled to one another by means of a rod, wherein the lever and the rod are coupled to one another.

6. The device of claim 2, wherein the control device is connected to a threaded rod in a rotationally fixed manner, wherein the first and second pistons have an internal thread, and the device is configured and arranged so that the pistons shift on the threaded rod with respect to the first hollow cylinder and the second hollow cylinder.

7. The device of claim 2, wherein the control device has an internal thread, wherein the first piston and the second piston are fixedly connected to a threaded rod, wherein the device is configured and arranged so that the threaded rod with the pistons shifts with respect to the control device and the hollow cylinders by means of the control device.

8. The device of claim 2, wherein a rod is arranged in a rotationally fixed manner with respect to a control device, but axially shiftable inside the control device, wherein the pistons are fixedly connected to the rod and at least one of the first and second hollow cylinders has an internal thread, wherein at least one of the first and second pistons engages with the internal thread of the at least one of the first and second hollow cylinders by means of an external thread or at least one pin, wherein the device is configured and arranged so that the rod with the pistons shifts with respect to the cylinders and the control device by means of the control device.

9. The device of claim 2, wherein the device is configured and arranged so that $\Delta V1$, $\Delta V2$ can be effected in the storage chambers with equal or unequal size.

10. The device of claim 1, wherein the child-proof lock is further configured and arranged to release the control device when the device is in a release state and otherwise block the control device.

11. The device according to claim 1, having a shell element, which is provided for accommodating an electric cigarette and which is set up to define the position and alignment of an electric cigarette in one, two, three, four, five or six degrees of freedom.

12. A system comprising:

a device including a first storage chamber configured and arranged for accommodating a consumable material, a second storage chamber configured and arranged for accommodating an equalizing fluid, an interface with first and second connections, the first connection fluidically connected to the first storage chamber and the second connection fluidically connected to the second storage chamber, and wherein the device is configured and arranged so that a change of volume within the first and second storage chambers are inversely related by means of a control device;

the first connection is configured and arranged for facilitating filling of the consumable material, and the second connection is configured and arranged for discharging the equalizing fluid; and a child-proof lock, which is provided with a bolt configured and arranged for blocking and releasing the control device;

wherein the child-proof lock is configured and arranged to release the control device when the device and a consumable material tank are in a filling position with respect to one another, and the child-proof lock otherwise blocks the control device.

13. A method for filling a consumable material tank of an electric cigarette by means of a device for filling the electric cigarette, having the step:

controlling a control device, whereby consumable material is filled from the device into the tank of the electric cigarette, characterized in that an equalizing fluid volume, which is displaced by the consumable material, which is filled in, is simultaneously extracted from the tank of the electric cigarette.

14. The method according to claim 13, further having the steps:

docking the device to the electric cigarette, whereby the control device is released, and undocking the device from the electric cigarette, whereby the control device is blocked.

15. A method for filling a consumable material tank of an electric cigarette by means of a device for filling the electric cigarette, having the steps:

fluidically connecting the consumable material tank to a first storage chamber, which is filled with a consumable material, fluidically connecting the consumable material tank to a second storage chamber, volume reduction of the first storage chamber, so that the consumable material reaches from the first storage chamber into the consumable material tank, and volume increase of the second storage chamber, so that an equalizing fluid, in particular air, is extracted from the consumable material tank into the second storage chamber.

16. A device comprising:

a first storage chamber configured and arranged for accommodating a consumable material, an interface, which is connected to a first connection, which is fluidically connected to the first storage chamber, characterized by a second storage chamber configured and arranged for accommodating an equalizing fluid, and a control device, wherein the device is configured and arranged to fill an electric cigarette in a manner so that the volumes of the first storage chamber and of the second storage chamber are changed in the opposite direction by means of the control device, and wherein the interface has a second connection, which is fluidically connected to the second storage chamber, wherein the first and the second storage chambers have a joint hollow cylinder and a piston positioned within the joint hollow cylinder, the piston configured and arranged to facilitate the $\Delta V1$, $\Delta V2$ via motion within the joint hollow cylinder; wherein the control device has a threaded rod comprising an external thread and the piston has an internal thread.

17. A device comprising:

a first storage chamber configured and arranged for accommodating a consumable material, an interface, which is connected to a first connection, which is fluidically connected to the first storage chamber, characterized by a second storage chamber configured and arranged for accommodating an equalizing fluid, and a control device, wherein the device is configured and arranged to fill an electric cigarette wherein the volumes of the first storage chamber and of the second storage chamber are changed in the opposite direction by means of the control device, and wherein the interface has a second connection, which is fluidically connected to the second storage chamber, wherein the first connection has a first cannula and the second connection has a second cannula.

\* \* \* \* \*